(12) United States Patent
Pfeiffer et al.

(10) Patent No.: US 11,957,845 B2
(45) Date of Patent: *Apr. 16, 2024

(54) MODULAR CATHETER

(71) Applicant: Medtronic Vascular, Inc., Santa Rosa, CA (US)

(72) Inventors: Ronja F. Pfeiffer, Galway (IE); Declan P. Costello, Ballinrobe (IE); Edmond Sheahan, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/120,314

(22) Filed: Mar. 10, 2023

(65) Prior Publication Data

US 2023/0201526 A1    Jun. 29, 2023

Related U.S. Application Data

(62) Division of application No. 17/144,336, filed on Jan. 8, 2021, now Pat. No. 11,628,272.

(60) Provisional application No. 62/970,534, filed on Feb. 5, 2020.

(51) Int. Cl.
*A61M 25/00*    (2006.01)

(52) U.S. Cl.
CPC .... *A61M 25/0053* (2013.01); *A61M 25/0097* (2013.01)

(58) Field of Classification Search
CPC .. A61F 2/95; A61F 2/2427; A61F 2220/0025; A61F 2002/30329; A61M 25/005; A61M 25/0054; A61M 25/01; A61M 25/0133; A61M 25/0144; A61M 25/0116
See application file for complete search history.

(56) References Cited

U.S. PATENT DOCUMENTS

| | | | |
|---|---|---|---|
| 4,483,562 A | 11/1984 | Schoolman | |
| 5,399,164 A * | 3/1995 | Snoke | A61M 25/0136 604/524 |
| 6,203,447 B1 | 3/2001 | Dillard | |
| 2008/0051705 A1 | 2/2008 | Von Oepen et al. | |
| 2008/0200874 A1* | 8/2008 | Ferry | A61M 25/0108 604/524 |
| 2012/0029281 A1 | 2/2012 | Frassica et al. | |
| 2012/0197239 A1 | 8/2012 | Smith et al. | |

(Continued)

OTHER PUBLICATIONS

PCT International Search Report and Written Opinion for International Application No. PCT/US2021/016496 dated May 11, 2021.

*Primary Examiner* — Tiffany Legette
*Assistant Examiner* — Phoebe Anne Staton
(74) *Attorney, Agent, or Firm* — Wentsler LLC

(57) ABSTRACT

Catheters include first and second segments that each include a proximal end and a distal end. A first connector of each catheter includes a first portion connected to the distal end of the first segment and a second portion connected to the proximal end of the second segment. The first portion and the second portion are engaged so that the first portion can rotated relative to the second portion about an axis of the first connector. The first segment and the second segment can bend in multiple planes via a rotation of the first portion relative to the second portion about the axis.

20 Claims, 3 Drawing Sheets

(56) References Cited

U.S. PATENT DOCUMENTS

| | | | |
|---|---|---|---|
| 2014/0222046 A1* | 8/2014 | Schneider | A61B 17/320783 |
| | | | 606/159 |
| 2017/0165064 A1* | 6/2017 | Nyuli | A61F 2/2436 |
| 2018/0235657 A1* | 8/2018 | Abunassar | A61M 25/0054 |
| 2019/0175375 A1 | 6/2019 | Schreck | |

* cited by examiner

MODULAR CATHETER

RELATED APPLICATIONS

This application is a divisional of U.S. application Ser. No. 17/144,336, filed Jan. 8, 2021, which claims the benefit of U.S. Provisional Patent Application No. 62/970,534, filed Feb. 5, 2020, the entire contents of which are incorporated herein by reference.

FIELD

The present technology is generally related to catheters for delivery of a prosthesis.

BACKGROUND

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be restored (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

A delivery catheter must often navigate through tortuous anatomy as it is tracked through the vasculature to the treatment site within the heart. The catheter may be navigated through various anatomical turns as it travels within the vasculature, including the sharp bend of the aortic arch.

The present disclosure addresses problems and limitations associated with the related art.

SUMMARY

The techniques of this disclosure generally relate to a catheter for use in delivering a prosthesis via percutaneous transcatheter (or transluminal) techniques. It is desirable that the clinician have the ability to accurately steer or deflect the catheter as it is guided and advanced to the treatment site. Embodiments of the disclosure achieve deflection of a delivery catheter as it navigates the anatomy of the vasculature while advancing to a desired treatment site.

In one aspect, the present disclosure provides a catheter including a plurality of a segments, each segment having a stiffener extending along its length. The plurality of segments are interconnected with connectors such that each of the segments can bend in multiple planes via rotation of the connectors.

In another aspect, the disclosure provides a catheter including a first tubular segment having a distal end and a proximal end; the first tubular segment further having a body and a set of spine wires longitudinally arranged with respect to the body. The catheter further includes a second tubular segment having a distal end and a proximal end; the second tubular segment further having a body and a set of spine wires longitudinally arranged with respect to the body. The catheter also includes a first connector having a first portion connected to the distal end of the first tubular segment and a second portion connected to the proximal end of the second tubular segment; wherein the first portion and the second portion are engaged so that the first and second portions can rotate with respect to each other.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
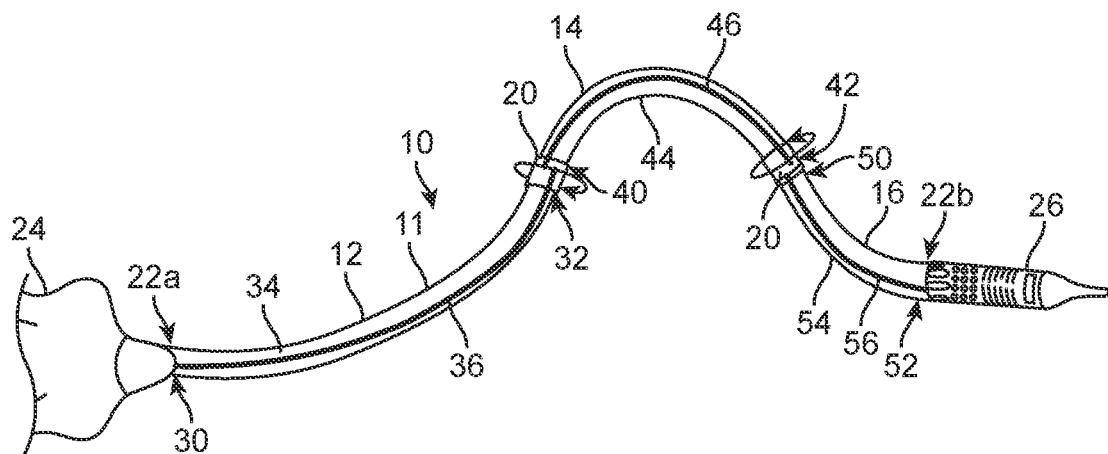
FIG. 1 is a conceptual diagram of a catheter having a plurality of tubular segments interconnected by connectors.
Figure 2:
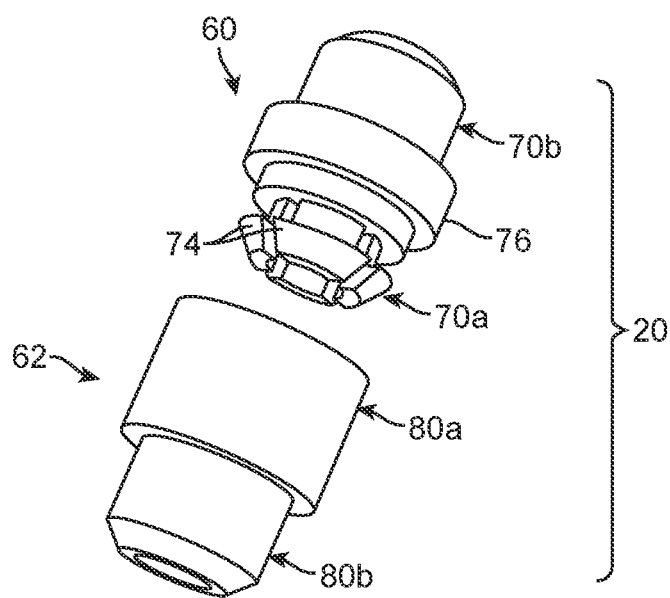
FIG. 2 is an exploded view of one connector of FIG. 1 having a first portion and a second portion.
Figure 3:
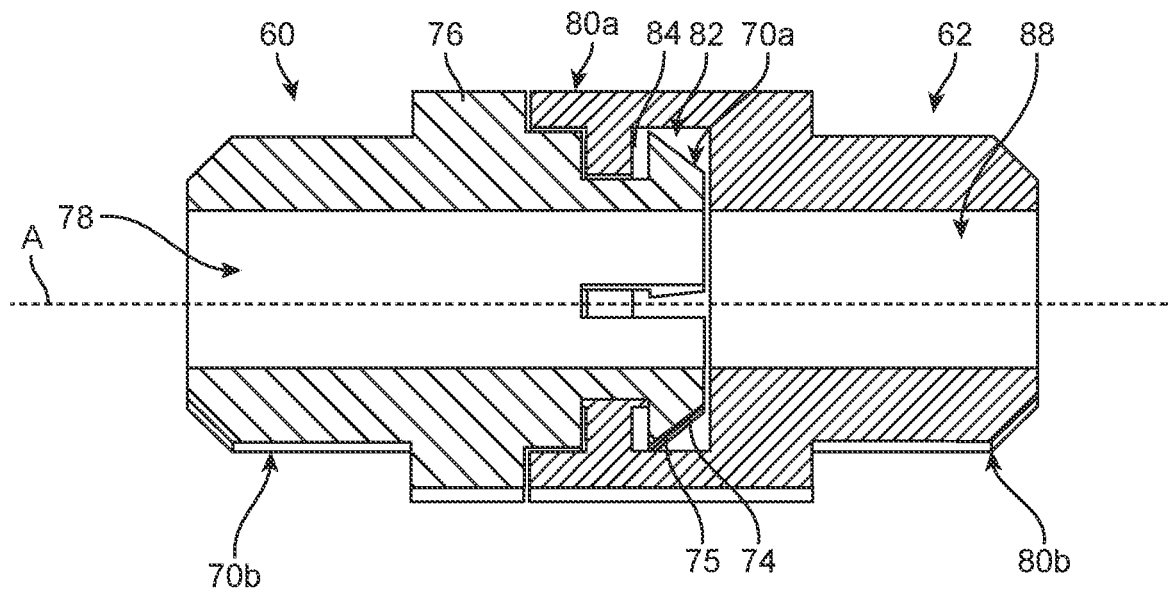
FIG. 3 is a cross-sectional view of the connector of FIG. 2.
Figure 4:
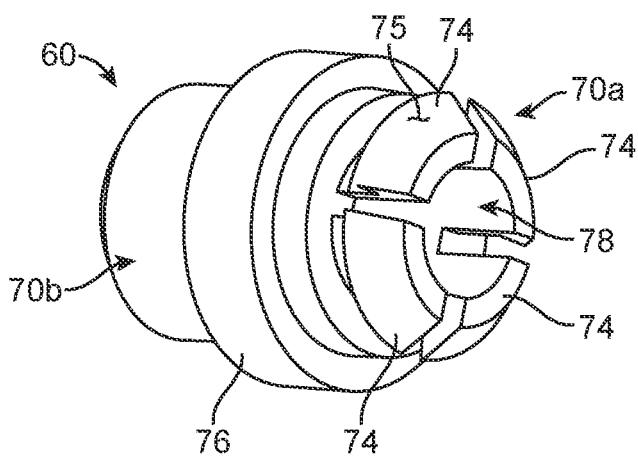
FIG. 4 is a perspective view of the first portion of the connector of FIGS. 1-3.
Figure 5:
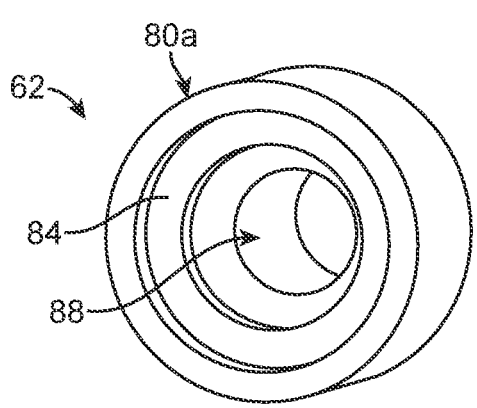
FIG. 5 is a perspective view of the second portion of the connector of FIGS. 1-3.

FIGS. 1-5 collectively illustrate a catheter 10 including a plurality of tubular segments 12, 14, 16 interconnected by connectors or torque relief nodes 20. The catheter 10 can be of the type for delivering a prosthesis (not shown) via percutaneous transcatheter (or transluminal) techniques. In such embodiments, at a proximal end 22a, the catheter 10 can include a handle assembly 24. At a distal end 22b, the catheter 10 can include a capsule 26 for compressively containing the prosthesis positioned therein. During such transcatheter techniques, it is typical for the catheter 10 to navigate through a series of bends in different planes and to deploy and recapture a prosthesis often requires a catheter that is sufficiently stiff with respect to tension and compression while maintaining a low bending stiffness, which is uniform around its circumference. Embodiments of the disclosure provide the required stiffness in tension and compression while also providing bending of the catheter in multiple planes. This bending function results in increased ability for the catheter to track through tortuous anatomies with bends in multiple planes and a reduced track force (i.e. reduced trauma to the patient).

In one example, the catheter 10 includes a first tubular segment 12 having a proximal end 30 and a distal end 32. The first tubular segment 12 further has a body 34 and a set of stiffeners 36 (e.g., spine wires) longitudinally arranged with respect to the body 34. Only one stiffener 36 is visible in FIG. 1, however, additional stiffeners can be positioned around the body 34, as desired. The catheter 10 also includes a second tubular segment 14 having a proximal end 40 and a distal end 42. The second tubular segment 14 further has a body 44 and a set of spine wires 46 longitudinally arranged with respect to the body 44 (only one spine wire 46 is visible as with segment 12). In the illustrated example, the catheter 10 optionally further includes a third tubular segment 16 having a proximal end 50 and a distal end 52. The third tubular segment 16 further has a body 54 and a set of spine wires 56 longitudinally arranged with respect to the body 54 (only one spine wire 56 is visible as with segment 12). All segments 12, 14, 16 can optionally be identically configured or can vary in configuration. In some embodiments, the catheter 10 includes additional tubular segments (e.g., between 2-10 segments), as desired, and the present disclosure is not intended to be limited to a particular number of tubular segments.

As previously indicated, one or more of the tubular segments 12, 14, 16 includes two spine wires 36, 46, 56 extending along a length of the respective tubular segment 12, 14, 16. In one example, each spine wire 36, 46, 56 extends and entire length of the respective tubular segment 12, 14, 16. The spine wires 36, 46, 56 are coaxial with a center axis of the respective tubular segment 12, 14, 16 and can be embedded within the respective body 34, 44, 54 of the respective tubular segment 12, 14, 16 or otherwise attached to the respective body 34, 44, 54. The spine wires 36, 46, 56 have a stiffness greater than a stiffness of the body 34, 44, 54 to support the body to resist compression, while allowing the body to bend. In one example, the spine wires 36, 46, 56 of a particular tubular segment 12, 14, 16 are positioned about 180 degrees (+/−5 degrees) about a circumference of the body 34, 44, 54.

To provide bending of the catheter 10 in multiple planes, two tubular segments 12, 14, 16 are interconnected with one connector 20 interconnecting two respective tubular segments. In the example of FIG. 1, the first and second tubular segments 12, 14 are interconnected with one connector 20 and the second and third tubular segments 14, 16 are interconnected with a second connector 20. As indicated with like reference numerals, it is to be understood that each connector 20 provided in the catheter 10 can be identically configured. In some embodiments, the connectors 20 provided can vary with respect to each other in ways described herein, for example. Each connector 20 includes a first portion 60 and a second portion 62. In on example, the first portion 60 is connected to the distal end 32 of the first tubular segment 12 and the second portion 62 is connected to the proximal end 40 of the second tubular segment 14. The first portion 60 and the second portion 62 are engaged so that the first and second portions 60, 62 can rotate about their joint central axis A with respect to each other. In one example, the first and second portions 60, 62 can rotated 360 degrees with respect to each other. In this way, the tubular segments 12, 14 of the catheter 10 can rotate relative to each other to navigate tortuous anatomy. It will be understood that the distal/proximal order of the first and second portions 60, 62 can be reversed as shown in FIGS. 6-7, for example.

One example of suitable connector 20 is shown in greater detail in FIGS. 2-5. The first portion 60 includes a first end 70a having a plurality of collet segments 74 (two of which are referenced for ease of illustration). The first portion 60 is shown as having four collet segments 74, however, more or fewer collet segments are envisioned. The collet segments 74 are connected to a mid portion 76. A second end 70b of the first portion 60 is configured to support and receive one end of one tubular segment and can optionally have a beveled surface. The mid portion 76 can have a larger outer diameter as compared to an outer diameter of the second end 70b for the end of the respective tubular segment to abut against. In one example, the first portion 60 further includes a central aperture 78 extending from the first end 70a to the second end 70b.

The second portion 62 includes a first end 80a having a receiving aperture 82 in which the collect segments 74 can be inserted and rotatingly retained therein via a ridge 84. In one example, the collet segments each include a ramped surface 75. Each of the collect segments 74 can be compressed toward axis A to slide past ridge 84. Once in receiving aperture 82, the collect segments 74 snap back away from axis A (see, in particular, FIG. 3). In one example, the first end 80a of the second portion 62 abuts against the mid portion 76 when the first and second portions 60, 62 are engaged. A second end of the second portion 62 is configured to support and receive one end of one tubular segment and can optionally have a beveled surface. In one example, the second portion 62 includes a central aperture 88 extending from the first end 80a to the second end 80b and in communication with the receiving aperture 82. In one example, the central aperture 88 has a diameter equal that the central aperture 78. The connector 20 is provided merely as one example and other connectors suitable for connecting two tubular segments and allowing rotation of the tubular segments about each other are also considered within the scope of the present disclosure.

Figure 6:
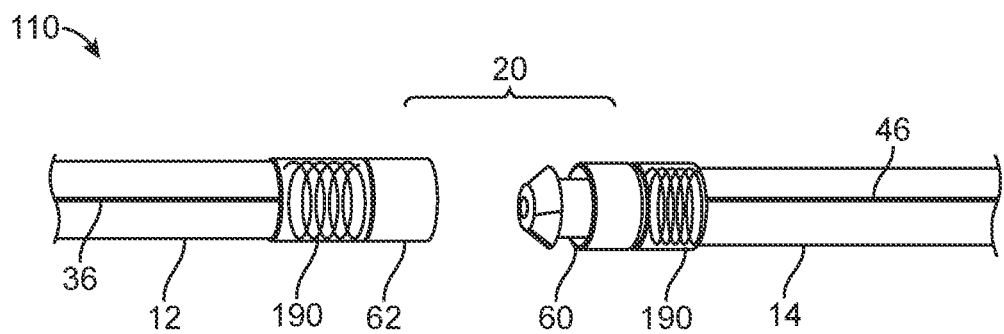
FIG. 6 is a partial, exploded side view of an alternate catheter.
Figure 7:
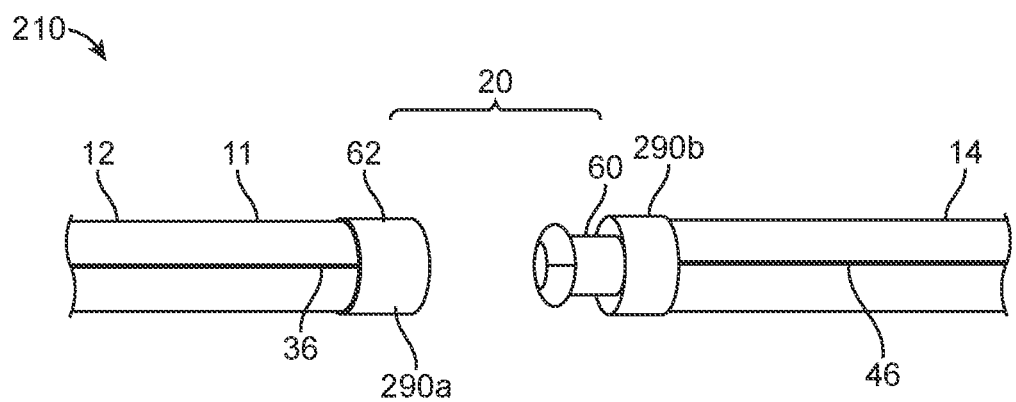
FIG. 7 is a partial, exploded side view of an alternate catheter.

Referring now in addition to FIG. 6, which illustrates a portion of an alternative catheter 110 that includes a first multi-filar coil 190 secured to the first tubular segment 12 adjacent to and connected to the second portion 62 of the connector 20 and a second multi-filar coil 190 secured to the second tubular segment 14 adjacent to and connected to the first portion 60 of the connector 20. The multi-filar coils 190 create a section of increased flexibility to minimize the stress concentrated at these locations of the catheter 110. As at least partially indicated with like reference numerals, the catheter 110 of FIG. 6 is otherwise identical to and operates similar to catheter 10 disclosed above unless explicitly stated.

Similarly, FIG. 7 illustrates a portion of an alternative catheter 210 that includes a first jacket 290a secured to the first tubular segment 12 adjacent to the first portion of the connector 20 and a second jacket 290b secured to the second tubular segment 14 adjacent to the first portion 60 of the connector 20. Each jacket 290a, 290b creates a section of increased stiffness/durometer to minimize the stress concentrated at the location of the respective jacket. In one example, one or more the jackets 290a, 290b has a variable stiffness/durometer. For example, the stiffness of each jacket 290a, 290b may increase in the direction of the connector 20. As at least partially indicated with like reference numerals, the catheter 210 of FIG. 7 is otherwise identical to and operates similar to catheter 10 unless explicitly stated.

In one example, a catheter was tested using a compound bend box having three 180 degree bends in different planes. A catheter having two spine wires but not including any connectors disclosed herein got stuck after the first bend due to the spine wires limiting the catheter to one plane of bending. In a second test, a catheter including a connector herein allowed the tubular segments of the catheter rotate in different planes, which enabled the catheter to go through the second bend before getting stuck in the compound bend box. The tested catheter of the disclosure traveled approximately 130 mm further through the compound bend box.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A catheter comprising:
   a first segment comprising a distal end and a proximal end;
   a second segment comprising a distal end and a proximal end; and
   a first connector comprising a first portion connected to the distal end of the first segment and a second portion connected to the proximal end of the second segment,
   wherein the first portion and the second portion are engaged so that the first portion can be rotated 360 degrees relative to the second portion about an axis of the first connector, and wherein the first segment and the second segment can bend in multiple planes by a rotation of the first portion relative to the second portion about the axis.

2. The catheter of claim 1, wherein the first segment comprises a stiffener extending along a length of the first segment between the distal end of the first segment and the proximal end of the first segment.

3. The catheter of claim 2, wherein the first segment comprises a first tubular segment comprising a body.

4. The catheter of claim 3, wherein the stiffener of the first segment comprises a set of spine wires longitudinally arranged with respect to the body.

5. The catheter of claim 4, wherein the set of spine wires of the first segment comprises a stiffness greater than a stiffness of the body of the first segment.

6. The catheter of claim 1, further comprising a capsule connected to the distal end of the second segment, the capsule configured to receive a prosthesis.

7. The catheter of claim 1, wherein at least one of the distal end of the first segment or the proximal end of the second segment comprises a jacket.

8. The catheter of claim 7, wherein the jacket comprises a varying durometer.

9. The catheter of claim 8, wherein the durometer is greatest adjacent the first connector.

10. The catheter of claim 1, wherein the first segment is overmolded to the first portion of the first connector.

11. The catheter of claim 1, wherein the first and second portions of the first connector are rotatably connected together by a snap-fit.

12. The catheter of claim 1, further comprising:
    a third segment comprising a distal end and a proximal end; and
    a second connector comprising a first portion connected to the distal end of the second segment and a second portion connected to the proximal end of the third segment,
    wherein the first portion and the second portion of the second connector are engaged so that the first portion of the second connector can rotated relative to the second portion of the second connector about an axis of the second connector, and wherein the second segment and the third segment can bend in multiple planes by a rotation of the first portion of the second connector relative to the second portion of the second connector about the axis of the second connector.

13. The catheter of claim 12, wherein the third segment comprises a stiffener extending along a length of the third segment between the distal end of the third segment and the proximal end of the third segment.

14. The catheter of claim 13, wherein the third segment comprises a third tubular segment comprising a body.

15. The catheter of claim 14, wherein the stiffener of the third segment comprises a set of spine wires longitudinally arranged with respect to the body of the third tubular segment.

16. The catheter of claim 12, wherein one of the first portion or the second portion of the second connector are engaged so that the first portion of the second connector can be rotated 360 degrees relative to the second portion of the second connector about the axis of the second connector.

17. A catheter comprising:
    a first segment comprising a distal end and a proximal end;
    a second segment comprising a distal end and a proximal end; and
    a first connector comprising a first portion connected to the distal end of the first segment and a second portion connected to the proximal end of the second segment,
    wherein the first portion and the second portion are engaged so that the first portion can be rotated relative to the second portion about an axis of the first connector, and wherein the first segment and the second segment can bend in multiple planes by a rotation of the first portion relative to the second portion about the axis, and at least one of the distal end of the first segment or the proximal end of the second segment comprises a multi-filar coil.

18. A catheter comprising:
    a first segment comprising a distal end and a proximal end;
    a second segment comprising a distal end and a proximal end; and
    a first connector comprising a first portion connected to the distal end of the first segment and a second portion connected to the proximal end of the second segment,
    wherein one of the first portion or the second portion of the first connector comprises a plurality of collet segments, and the first portion and the second portion are engaged so that the first portion can be rotated relative to the second portion about an axis of the first connector, and
    wherein the first segment and the second segment can bend in multiple planes by a rotation of the first portion relative to the second portion about the axis.

19. The catheter of claim 18, wherein the first portion comprises a receiving aperture and the second portion comprises the plurality of collet segments, wherein the plurality of collet segments are rotatingly maintained within the receiving aperture.

20. The catheter of claim 18, wherein the second portion comprises a receiving aperture and the first portion comprises the plurality of collet segments, wherein the plurality of collet segments are rotatingly maintained within the receiving aperture.

* * * * *